(12) United States Patent
Levy (10) Patent No.: US 12,171,437 B2
(45) Date of Patent: *Dec. 24, 2024

(54) SYSTEM AND METHOD FOR THE EFFECTIVE, RELIABLE AND FOOLPROOF DELIVERY OF EMBOLIC AGENTS

(71) Applicant: Frank Levy, Fort Myers, FL (US)

(72) Inventor: Frank Levy, Fort Myers, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/660,071

(22) Filed: Apr. 21, 2022

(65) Prior Publication Data
US 2022/0240943 A1    Aug. 4, 2022

Related U.S. Application Data

(60) Continuation of application No. 16/794,930, filed on Feb. 19, 2020, now Pat. No. 11,344,315, which is a
(Continued)

(51) Int. Cl.
*A61B 17/12* (2006.01)
*A61M 5/178* (2006.01)
(Continued)

(52) U.S. Cl.
CPC ......... *A61B 17/12186* (2013.01); *A61M 5/19* (2013.01); *A61M 39/223* (2013.01);
(Continued)

(58) Field of Classification Search
CPC ... A61B 17/12186; A61M 5/19; A61M 5/007; A61M 5/16827; A61M 39/22; A61M 39/223; A61M 39/225; A61M 2039/229
See application file for complete search history.

(56) References Cited

U.S. PATENT DOCUMENTS

| 3,004,686 A | 10/1961 | Mckee |
| 4,219,021 A | 8/1980 | Fink |

(Continued)

FOREIGN PATENT DOCUMENTS

| CN | 2179152 Y | 10/1994 |
| DE | 10161027 A1 | 6/2003 |

(Continued)

*Primary Examiner* — Dung T Ulsh (74) *Attorney, Agent, or Firm* — Welsh Flaxman & Gitler LLC (57) ABSTRACT

A delivery system for the delivery of embolic agents to a patient includes a control valve assembly interconnecting first, second, third and fourth conduits, wherein the control valve assembly selectively moves between first, second, and third states under the control of a medical professional. In the first state, the first conduit communicates with the second conduit for transmitting a solution of embolic agents between a first syringe secured to the first conduit and a second syringe secured to the second conduit. In the second state, the second conduit communicates with the third conduit for transmitting the solution of embolic agents from the second syringe to a delivery catheter secured to the third conduit. In the third state, the third conduit communicates with the fourth conduit for flushing the delivery catheter via a third syringe, which is filled with saline, connected to the fourth conduit.

9 Claims, 4 Drawing Sheets

Related U.S. Application Data division of application No. 15/015,557, filed on Feb. 4, 2016, now Pat. No. 10,610,232.

(60) Provisional application No. 62/113,806, filed on Feb. 9, 2015.

(51) Int. Cl.
- *A61M 5/19* (2006.01)
- *A61M 39/22* (2006.01)
- *A61M 39/24* (2006.01)

(52) U.S. Cl.
CPC ..... *A61M 39/24* (2013.01); *A61B 2017/1205* (2013.01); *A61M 2005/1787* (2013.01); *A61M 2039/229* (2013.01)

(56) References Cited

U.S. PATENT DOCUMENTS

| | | |
|---|---|---|
| 4,950,230 A | 8/1990 | Kendell |
| 5,135,026 A | 8/1992 | Manska |
| 5,195,963 A | 3/1993 | Yafuso et al. |
| 5,345,932 A | 9/1994 | Yafuso et al. |
| 5,830,178 A | 11/1998 | Jones |
| 6,315,762 B1 * | 11/2001 | Recinella ............. A61M 5/007 604/247 |
| 2001/0044618 A1 | 11/2001 | Recinella et al. |
| 2002/0017328 A1 | 2/2002 | Loo |
| 2003/0181850 A1 * | 9/2003 | Diamond ............. A61M 39/223 604/93.01 |
| 2005/0000981 A1 | 1/2005 | Peng et al. |
| 2006/0235297 A1 | 10/2006 | Kawamoto |
| 2007/0104616 A1 | 5/2007 | Keenan et al. |
| 2007/0111298 A1 | 5/2007 | Muller et al. |
| 2008/0167621 A1 | 7/2008 | Wagner et al. |
| 2009/0062741 A1 | 3/2009 | Smith et al. |
| 2009/0247985 A1 * | 10/2009 | Melsheimer .......... A61J 1/2096 604/506 |
| 2011/0152850 A1 | 6/2011 | Niedbala et al. |
| 2011/0218411 A1 | 9/2011 | Keenan et al. |
| 2012/0065502 A1 * | 3/2012 | Levy ...................... A61M 5/19 600/431 |
| 2015/0129061 A1 * | 5/2015 | Duncan ............... F16K 37/0008 137/553 |
| 2016/0228129 A1 | 8/2016 | Levy |
| 2017/0368254 A1 | 12/2017 | Levy et al. |

FOREIGN PATENT DOCUMENTS

| | | |
|---|---|---|
| EP | 2468204 A1 | 6/2012 |
| JP | H06013854 U | 2/1994 |

* cited by examiner

SYSTEM AND METHOD FOR THE EFFECTIVE, RELIABLE AND FOOLPROOF DELIVERY OF EMBOLIC AGENTS

CROSS REFERENCE TO RELATED APPLICATIONS

This application is continuation of U.S. patent application Ser. No. 16/794,930, filed Feb. 19, 2020, entitled "SYSTEM AND METHOD FOR EFFECTIVE, RELIABLE AND FOOLPROOF DELIVERY OF EMBOLIC AGENTS.", which is a division of U.S. patent application Ser. No. 15/015,557, filed Feb. 4, 2016, entitled "SYSTEM AND METHOD FOR EFFECTIVE, RELIABLE AND FOOLPROOF DELIVERY OF EMBOLIC AGENTS," which issued as U.S. Pat. No. 10,610,232, which claims the benefit of U.S. Provisional Patent Application Ser. No. 62/113,806, entitled "SYSTEM AND METHOD FOR THE EFFECTIVE, RELIABLE AND FOOLPROOF DELIVERY OF EMBOLIC AGENTS," filed Feb. 9, 2015.

BACKGROUND OF THE INVENTION

1. Field of the Invention

This invention relates to a system for safely and efficiently providing for embolic agent delivery.

2. Description of the Related Art

The major impediment to precise delivery and administration of embolic agents is dilution and suspension. As those skilled in the art appreciate, embolic agents are those materials used therapeutically as a treatment for bleeding or some types of cancer by deliberately blocking blood vessels.

Inappropriate solution and dilution can lead to premature aggregation and occlusion of the delivery catheter and/or target vessel. It can also lead to embolization at undesired locations within the vasculature. Current systems for the delivery of embolic agents require multiple pieces of equipment that must be connected/disconnected in a manner making delivery cumbersome and susceptible to spills.

For example, purging the delivery catheter with saline often requires removal of the delivery syringe which is cumbersome and time consuming. With appropriate dilution and solution, plus purging, a more-controlled precision delivery can be obtained, thereby lessening the chance for non-target embolization. Another big challenge in embolic agent delivery is in the use of the standard 3-way stopcock. In order for the physician to properly perform the procedure, it is common for them to disconnect syringes. This is cumbersome, especially when dealing with chemotherapy.

With the application of the Applicant's proprietary technology as previously described in U.S. patent application Ser. No. 13/857,448, which is incorporated herein by reference, it is possible to make the delivery of embolic agents more user-friendly and more precise, with less chance for complications. With the proprietary valve described in U.S. patent application Ser. No. 13/857,448, one is able to keep embolic products in suspension and deliver them more efficiently than ever before.

SUMMARY OF THE INVENTION

It is, therefore, an object of the present invention to provide a delivery system for the delivery of embolic agents to a patient. The delivery system includes a control valve assembly interconnecting first, second, third and fourth conduits, wherein the control valve assembly selectively moves between first, second, and third states under the control of a medical professional. In the first state, the first conduit communicates with the second conduit for transmitting a solution of embolic agents between a first syringe secured to the first conduit and a second syringe secured to the second conduit. In the second state, the second conduit communicates with the third conduit for transmitting the solution of embolic agents from the second syringe to a delivery catheter secured to the third conduit. In the third state, the third conduit communicates with the fourth conduit for flushing the delivery catheter via a third syringe, which is filled with saline, connected to the fourth conduit.

It is also an object of the present invention to provide a delivery system wherein while in the first state, the first and second conduits, and ultimately the first and second syringes, are isolated from the third and fourth conduits; while in the second state, the second and third conduits, as well as the second syringe and the patient, are isolated from the first conduit and fourth conduit; and while in the third state, the third and fourth conduits, as well as the patient and the third syringe, are isolated from the first conduit and second conduit.

It is another object of the present invention to provide a delivery system wherein the control valve assembly includes a valve body having selectively aligned first, second, third and fourth passageways that define the first, second, third and fourth conduits, respectively, to allow for the controlled application of embolic agents to a patient.

It is a further object of the present invention to provide a delivery system wherein a stopcock is rotatably mounted within the valve body and includes an angled channel having a pair of communicably interconnected channel segments interconnected at an angle that is generally equivalent to the angle formed between each adjacent pair of non-aligned first, second, third and fourth passageways in the valve body such that the stopcock is rotatable to align the channel segments with a selected adjacent pair of the first, second, third and fourth passageways to permit communication between those passageways in a highly controlled manner.

It is also an object of the present invention to provide a delivery system wherein the stopcock is selectively adjusted between first, second and third positions.

It is another object of the present invention to provide a delivery system wherein in the first position the channel segments communicably interconnect the first passageway defining the first conduit and the second passageway defining the second conduit for functioning accordance with the first state.

It is a further object of the present invention to provide a delivery system wherein in the second position the channel segments communicably interconnect the second passageway defining the second conduit and the third passageway defining the third conduit for functioning in accordance with the second state.

It is also an object of the present invention to provide a delivery system wherein in the third position the channel segments communicably interconnect the third passageway defining the third conduit and the fourth passageway defining the fourth conduit for functioning in accordance with the third state.

It is another object of the present invention to provide a delivery system wherein the third conduit includes a one-way valve for limiting flow to a single direction from a source to the patient and for preventing flow in an opposite direction.

It is a further object of the present invention to provide a delivery system wherein the fourth conduit includes a one-way valve and a fitting for selective and sealable connection of the third syringe.

It is also an object of the present invention to provide a method for the delivery of embolic agents to a patient. The method employs a flow control system composed of a control valve assembly that interconnects first, second, third and fourth conduits, the control valve assembly selectively moving between first, second, and third states under control of a medical professional. The method includes the steps of securing a first syringe containing a solution of embolic agents to the first conduit and securing a second syringe to the second conduit, securing a catheter to the third conduit, the catheter being deployed within a patient at a desired location, and securing a third syringe containing saline to the fourth conduit. With the control valve assembly in the first state, the method is performed by actuating the first syringe to force the solution of embolic agents to the second conduit and the second syringe. With the control valve assembly in the second state, the method is performed by actuating the second syringe to move the solution of embolic agents from the second syringe, through the second conduit and third conduit, and into the catheter and ultimately to the desired location within the patient. With the control valve assembly in the third state, the method is performed by actuating the third syringe to introduce saline from the third syringe into the catheter to flush any embolic agents therefrom.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

The present invention provides a delivery system 10 for the effective, reliable and foolproof delivery of controlled amounts of embolic agents to a patient. In accordance with the present invention, and with reference to the various figures, delivery is achieved through the utilization of a multi-part valve delivery system 10. The multi-part valve delivery system 10 delivers a solution of embolic agents and purging saline in precisely controlled amounts sequentially through a series of syringes 12, 14, 16 such that it is practically impossible to improperly deliver the medical fluids to the patient. At the same time, the various syringes 12, 14, 16 delivering the solution of embolic agents and the purging saline do not have to be disconnected and reconnected during the administration to the patient. This greatly reduces the intrusion of undesirable components into the medical fluids being delivered.

The delivery system 10 of this invention is particularly beneficial for delivering embolic agents, for example, embolic microspheres or embolic foam gel, for medical use. For example, it is appreciated embolic microspheres in the form of non-spherical polyvinyl alcohol (PVA) particles, spherical tris-acryl particles, or calibrated microspheres consisting of a hydrogel core of polymethylmethacrylate with a thin coating of polyzene-F in a saline solution are used in various procedures and may be used in accordance with the present invention. Similarly, it is appreciated embolic foam gel in the form of low density shape memory polymer foams are used in various procedures and may be used in accordance with the present invention. In medical uses, these embolic agents are used to create controlled embolization for various medical procedures, for example, gastro-intestinal bleeding, cancer treatment, and tumor treatment.

Figure 1:
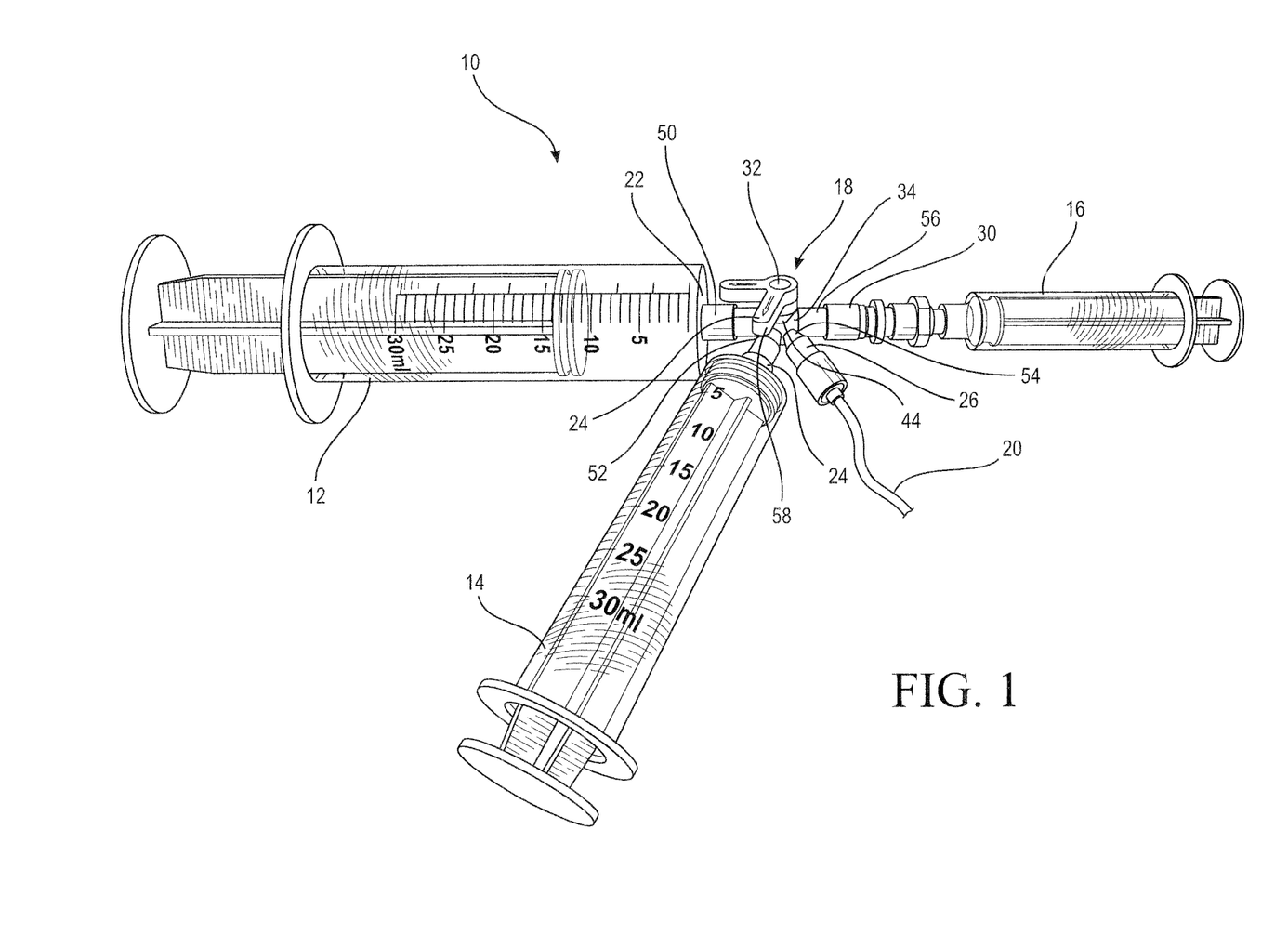
FIG. 1 is a perspective view of the present delivery system for embolic agents.
Figure 2:
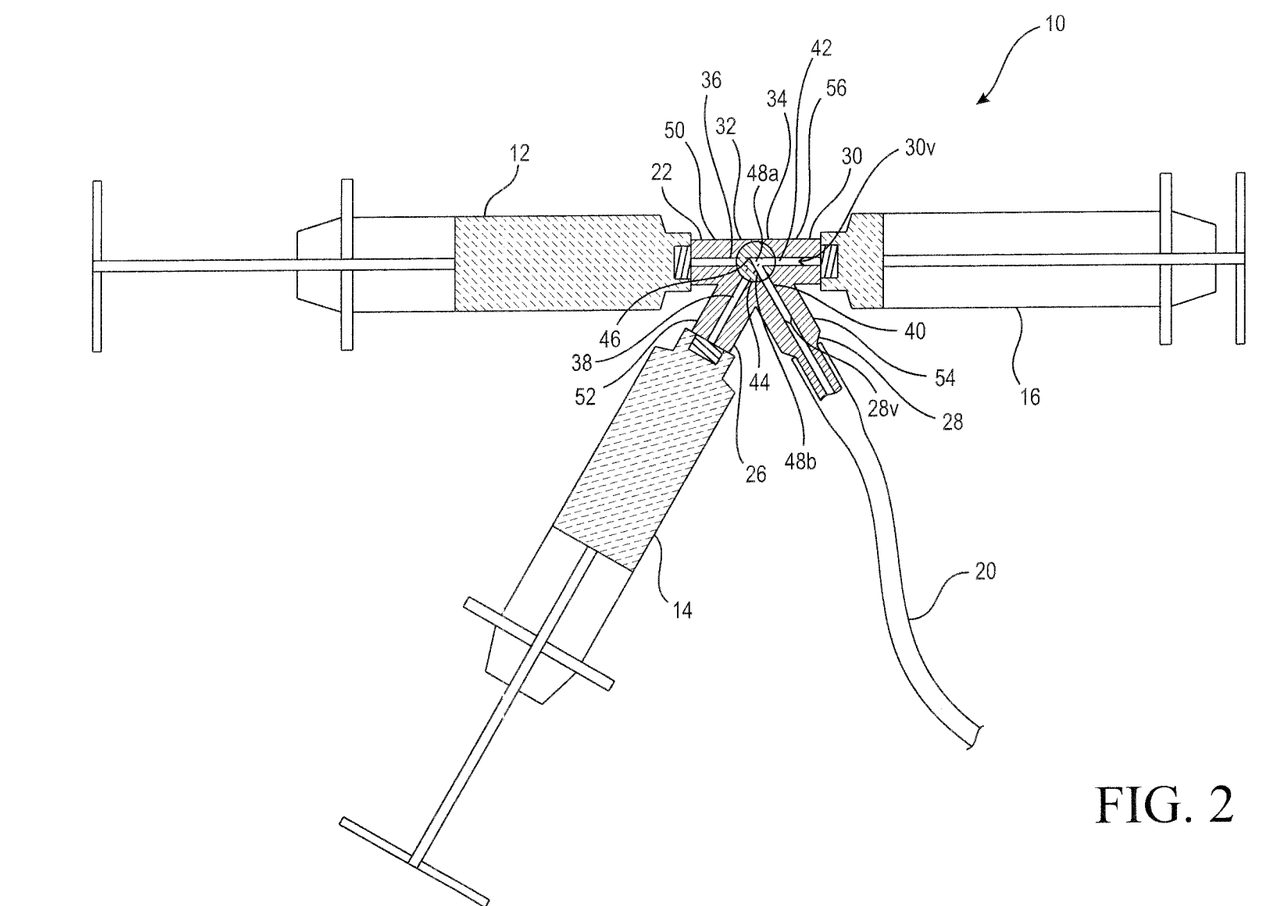
FIG. 2 is a schematic view of the present delivery system.
Figure 3:
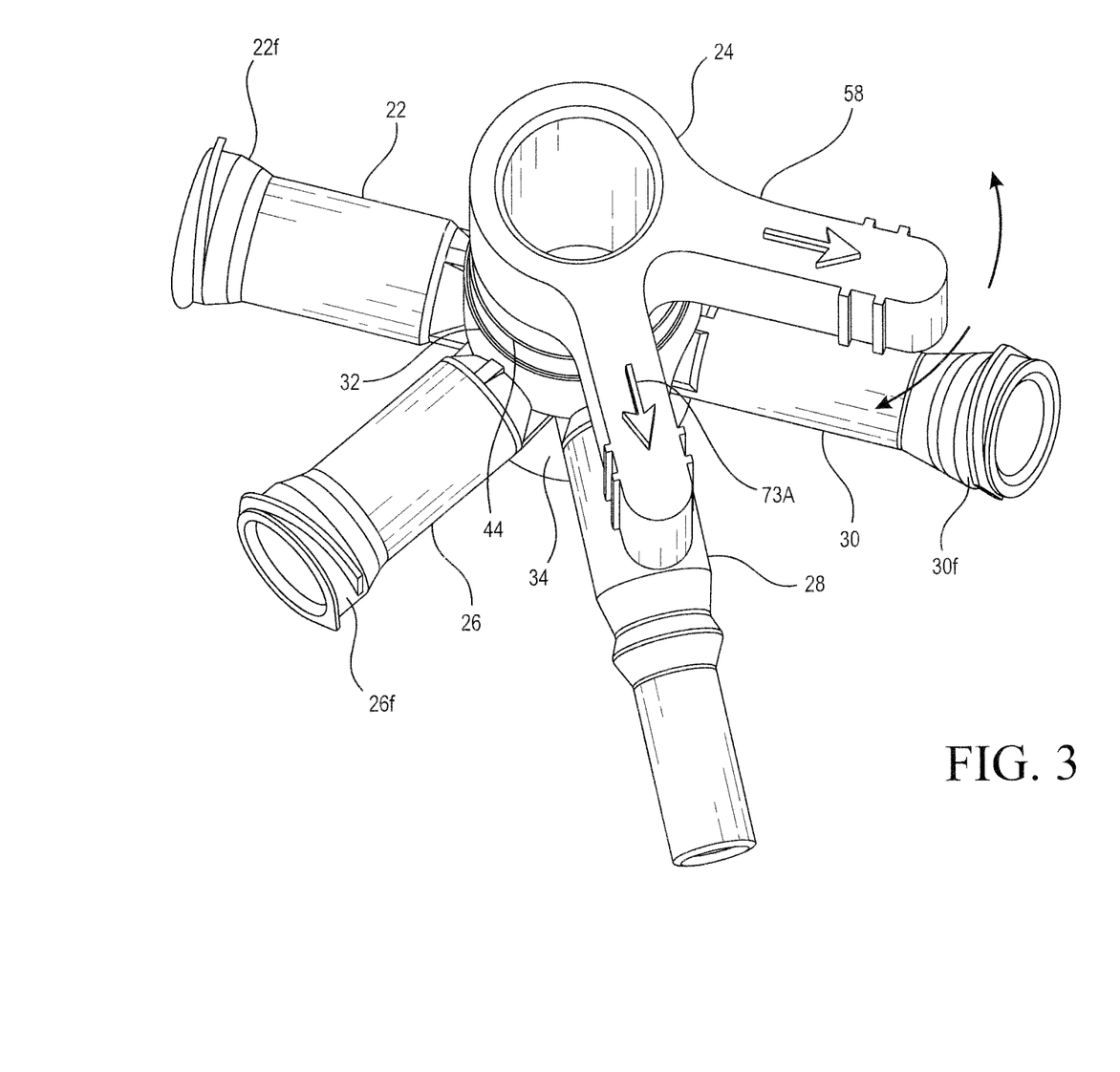
FIG. 3 is a perspective view of the control valve assembly of the present delivery system.
Figures 4A, 4B, 4C:
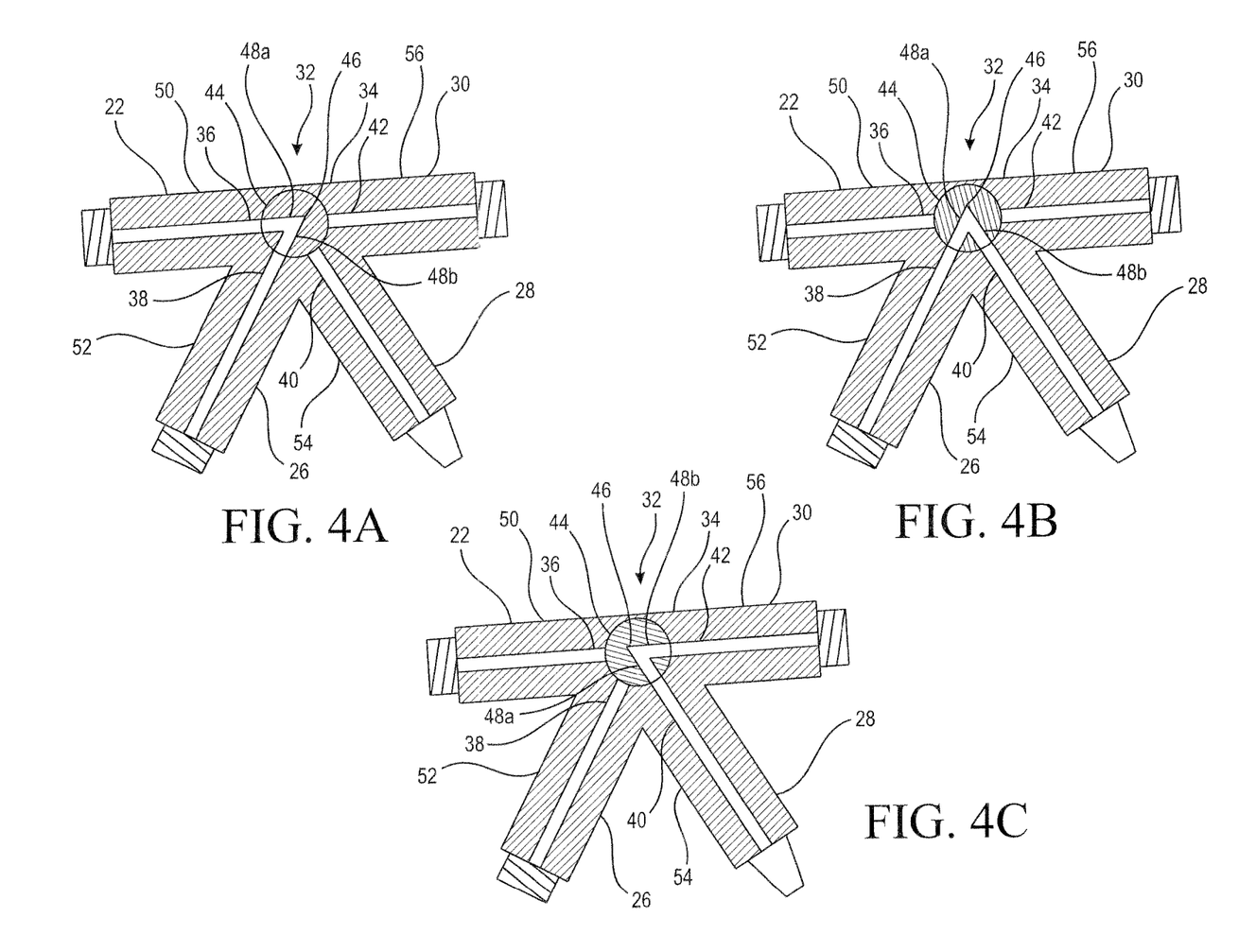
FIGS. 4A, 4B, and 4C are schematic views of the control valve assembly in the first, second and third positions, respectively.

The delivery of embolic agents is achieved through the utilization of the delivery system 10 as disclosed with reference to FIGS. 1 to 4. The present delivery system 10 provides an improved, foolproof mechanism for safely delivering controlled amounts of embolic agents to a patient utilizing a multi-part valve that delivers the embolic agents in precisely controlled amounts sequentially through a series of syringes 12, 14, 16 so as to reduce the possibility of improper solution preparation and dilution, minimize the potential for premature aggregation and occlusion of the delivery catheter 20 and/or target vessel, and improve purging of the delivery catheter 20 with saline. Ultimately, the present delivery system 10 makes the delivery of embolic agents more user-friendly and more precise, with less chance for complications.

The delivery system 10 provides for controlled delivery of embolic agents from a source of such embolic agents, for example, a first syringe 12 filled with a solution of embolic agents to a patient. Briefly, and as will be explained below in greater detail, the delivery system 10 includes a control valve assembly 32 interconnecting first, second, third and fourth conduits 22, 26, 28, 30 wherein the control valve assembly 32 selectively moves between first, second, and third states under the control of a medical professional for the controlled delivery of the embolic agents. The solution containing the embolic agents is connected to a first conduit 22 of the delivery system 10. With the stopcock 44 of the valve lever 58 of the control valve assembly 32 of the delivery system 10 in the first position (see FIG. 4A), the first and second syringes 12, 14, respectively connected to the first and second conduits 22, 26 of the delivery system 10, are manually and alternately actuated to push fluid between the two syringes 12, 14 in a manner agitating the embolic agent and enabling the embolic agent to remain in a suspended state within the solution as the solution is forced to move between the two syringes 12, 14. The stopcock 44 of the control valve assembly 32 of the delivery system 10 is then put into the second position (see FIG. 4B) to deliver the embolic agents contained within the second syringe 14 to the delivery catheter 20 secured to the third conduit 28 of the delivery system 10 and ultimately to a patient receiving fluid from the delivery catheter 20. When the embolic agents have been delivered, the stopcock 44 of the control valve assembly 32 of the delivery system 10 is then put into the third position (see FIG. 4C) enabling saline from a third syringe 16 coupled to the fourth conduit 30 of the delivery system 10 to flush the delivery catheter 20, preventing occlusion of the delivery catheter 20 with embolic agents remaining within the delivery catheter 20 and non-target embolization.

As briefly mentioned above, the delivery system 10 includes a control valve assembly 32 that interconnects the first, second, third and fourth conduits 22, 26, 28, 30. The control valve assembly 32 selectively moves between first, second, and third states under the control of a medical professional. In the first state, the first conduit 22 communicates with the second conduit 26 for transmitting the solution of embolic agents between the first syringe 12 secured to the first conduit 22 and the second syringe 14 secured to the second conduit 26. While in the first state, the first and second conduits 22, 26, and ultimately the first and second syringes 12, 14, are isolated from the third and fourth conduits 28, 30, as well as any structure connected thereto.

In the second state, the second conduit 26 communicates with the third conduit 28 for transmitting embolic agents from the second syringe 14 secured to the second conduit to the delivery catheter 20 secured to the third conduit and ultimately to the patient. In this way, the second syringe 14 secured to the second conduit 26 communicates with the patient via the delivery catheter 20 based upon the interconnection between the second conduit 26 and the patient outlet, third conduit 28. As with the first state, the second and third conduits 26, 28, as well as the second syringe 14, the delivery catheter 20 and the patient, are isolated from the first conduit 22 and fourth conduit 30.

In the third state, the third conduit 28 communicates with the fourth conduit 30 such that the third syringe 16, which is filled with saline, connected to the fourth conduit 30 communicates with the delivery (or outlet) catheter 20 secured to the third conduit (and the patient) to allow one to flush the delivery catheter 20 leading to the patient. As with the first and second states, the third and fourth conduits 28, 30, as well as the patient and the saline filled third syringe 16, are isolated from the first conduit 22 and second conduit 26.

In one embodiment, the control valve assembly 32 includes a valve body 34 having selectively aligned first, second, third and fourth passageways 36, 38, 40, 42 that define the first, second, third and fourth conduits 22, 26, 28, 30, respectively, to allow for the controlled application of embolic agents to a patient. A stopcock 44 is mounted rotatably within the valve body 34 and includes an angled channel 46 having a pair of communicably interconnected channel segments 48a, 48b that extend axially at an acute angle to one another. The channel segments 48a, 48b of the stopcock 44 are interconnected at an angle that is generally equivalent to the angle formed between each adjacent pair of non-aligned first, second, third and fourth passageways 36, 38, 40, 42 in the valve body 34 such that the stopcock 44 is rotatable to align the channel segments 48a, 48b with a selected adjacent pair of the first, second, third and fourth passageways 36, 38, 40, 42 (that is, the first, second, third and fourth conduits 22, 26, 28, 30) to permit medical fluids communication between those passageways in a highly controlled manner.

As explained above, the stopcock 44 is selectively adjusted between first, second and third positions. In the first position (see FIG. 4A), the channel segments 48a, 48b communicably interconnect the first passageway 36 defining the first conduit 22 and the second passageway 38 defining the second conduit 26. Embolic agents introduced through a first syringe 12 connected to the first conduit 22 may then be selectively transmitted between the first syringe 12 connected to the first conduit 22 and the second syringe 14 connected to the second conduit 26. In this way, the solution in which the embolic agents are to be delivered is moved so as to maintain the embolic agents in suspension by mechanical agitation within the solution prior to delivery to the patient. The solution may be pushed back and forth between the first and second syringes 12, 14 as desired until such a time that delivery to the patient is desired. The embolic agents are thereby transmitted between the first conduit 22 and the channel 46 of the stopcock 44 to the second conduit 26. This directs the embolic agents to a second syringe 14 attached thereto. In the second valve position (see FIG. 4B), the stopcock 44 aligns the channel segments 48a, 48b with the second and third passageways 38, 40 defining the second and third conduits 26, 28, respectively. This isolates the solution of embolic agents in the second syringe 14 from both the first and fourth conduits 22, 30. The second syringe 14 is operated to direct the solution of embolic agents through the second conduit 26, the stopcock channel 46 and the third conduit 28 into the delivery catheter 20 joined to the patient. In the third valve position (see FIG. 4C), the stopcock 44 is rotated to align the channel segments 48a, 48b with the third passageway 40 and the fourth passageway 42 defining the third conduit 28 and fourth conduit 30, respectively. This isolates the embolic agents in the delivery catheter 20 and the patient from the first syringe 12 secured to the first conduit 22 and the second syringe 14 secured to the second conduit 26. The third syringe 16 secured to the fourth conduit 30 is then operated to drive saline within the third syringe 16 through the fourth conduit 30, the channel 46 of the stopcock 44 and the delivery (or outlet) catheter 20 at the third conduit 28.

The first and second conduits 22, 26 preferably include fittings 22f, 26f, for example, Luer fittings, for selectively connecting the first syringe 12 containing a solution of embolic agents and the second syringe 14 to the control valve assembly 32. The third conduit 28 includes a one-way valve 28v for limiting the flow of embolic agents or saline to a single direction from the source of either the solution of embolic agents or saline to the patient and for preventing flow in the opposite direction. As for the fourth conduit 30 it includes both a one-way valve 30v and a fitting 30f, for example, a Luer fitting, for selective and sealable connection of the third syringe 16 with the control valve assembly 32. The one-way valve 30v of the fourth conduit 30 limits the flow of saline from the third syringe 16 to a single direction from the third syringe 16 to the delivery catheter 20 and patient, while preventing flow in the opposite direction.

The three-stage control valve assembly 32 includes a generally K-shaped valve body 34, which is preferably composed of various medical grade plastics, metals and/or metal alloys. Typically, the valve body 34 includes a molded or otherwise unitary construction. More particularly, the valve body 34 includes aligned first, second, third and fourth branches 50, 52, 54, 56 which respectively include the previously discussed internal first, second, third and fourth passageways 36, 38, 40, 42. Each of the first, second, third and fourth branches 50, 52, 54, 56, as well as the first, second, third and fourth passageways 36, 38, 40, 42, extends at an angle of substantially 60 degrees relative to the adjacent branches (or passageways) of the valve body 34.

In particular, the first and second branches 50, 52 (and passageways 36, 38) extend at an angle of substantially 60 degrees to one another, the second and third branches 52, 54 (and passageways 38, 40) extend at an angle of substantially 60 degrees to one another, and the third and fourth branches 54, 56 (and passageways 40, 42) extend at an angle of substantially 60 degrees to one another. Accordingly, the first and fourth branches 50, 56 (and passageways 36, 42) are substantially aligned and form a 180 degrees angle.

Accordingly, the angled channel 46 of the stopcock 44 includes communicably interconnected channel segments 48a, 48b having respective longitudinal axes that extend at an angle of approximately 60 degrees to one another. As used herein, "approximately 60 degrees" should be understood to mean that the angle formed between the respective longitudinal axes of the channel segments 48a, 48b is substantially equivalent to the angle formed between the longitudinal axes of respective pairs of the non-aligned adjacent passageways 36, 38, 40, 42 of valve body 34 (e.g. respective pairs of passageways). This enables the channel segments 48a, 48b to be communicably aligned with a selected pair of the passageways 36, 38, 40, 42 in the manner described more fully herein. It should be understood that in alternative embodiments the passageways and channel segments may have other corresponding angles. This is particularly applicable when the intake and discharge passageways and/or the inlet and outlet conduits are not aligned.

A valve lever 58 is mounted to the valve body 34 (in particular, to the stopcock 44) for selectively rotating the stopcock 44 into a selected one of three positions. Such selective positioning of the stopcock 44 provides for controlled multiple stage delivery of embolic agents through the control valve assembly 32 from the first conduit 22 to the outlet third conduit 28. This operation is described more fully below.

The delivery system 10 is operated to deliver embolic agents to a patient in a controlled and extremely safe and reliable manner. This operation is performed as follows. The first syringe 12 containing the solution of embolic agents is secured to the first conduit 22 and the second syringe 14 (which may contain saline or additional medicine to be mixed with the solution of embolic agents) is secured to the second conduit 26. The patient outlet, third conduit 28 likewise is communicably interconnected with the delivery catheter 20 that is deployed within a patient at a desired location. Finally, the third syringe 16 containing saline is secured to the fourth conduit 30.

After control valve assembly 32 has been interconnected with the patient and the various syringes 12, 14, 16, the stopcock 44 is operated by the valve lever 58 to align the channel segments 48a, 48b of the stopcock channel 46 with the passageways 36, 38, 40, 42 (and conduits 22, 26, 28, 30) respectively. With the valve lever 58 in the first position (see FIG. 4A), the first syringe 12 may be actuated to force the solution of embolic agents to the second conduit 26 and the second syringe 14. The first and second syringes 12, 14 may then be actuated to move the solution therebetween as desired. It is appreciated the specific manner in which the first and second syringes 12, 14 are actuated is determined based upon the specific composition of the embolic agent and such agitation of the embolic agent is performed in a manner that maintains the embolic agent in suspension such that it functions in a desirable manner when delivered to the patient.

Once it is desired to deliver the solution of embolic agents to the patient, the second syringe 14 is filled to a desired level and the valve lever 58 is moved to its second position (see FIG. 4B) aligning the channel segments 48a, 48b of the stopcock channel 46 with the second and third passageways 38, 40 (and conduits 26, 28), and isolating the other passageways and conduits therefrom. The second syringe 14 may then be depressed to move solution from the second syringe 14, through the channel segments 48a, 48b of the of the stopcock channel 46, into the delivery catheter 20 and ultimately to a desired location within the patient. It should appreciated the solution of embolic agents are delivered through the one-way valve 28v of the third conduit 28 and the one-way valve 28v prevents backflow of embolic agents.

Once the solution of embolic agents is fully delivered, the valve lever 58 is moved to its third position (see FIG. 4C) aligning the channel segments 48a, 48b of the stopcock channel 46 with the third and fourth passageways 40, 42 (and conduits 28, 30), and isolating the other passageways and conduits therefrom. At this point, saline from the third syringe 16 may be introduced into the delivery catheter 20 to flush any embolic agents therefrom so as to prevent undesired accumulation of the embolic agents therein. The one-way valves 28v, 30v of the third and fourth conduits 28, 30 prevent backflow of the saline.

It is appreciated the lever 58 may be configured as an arrow or otherwise marked to include an arrow that points in the direction of the intended embolic agents flow. Accordingly, the present delivery system 10 enables controlled amounts of embolic agents to be delivered to the patient in a safe and reliable manner. After the components are connected, they may remain connected during the entire medical procedure and do not then have to be disconnected and reconnected. This minimizes the possibility that air will intrude into the system and endanger the patient. Controlled and precise dosages of embolic agents are delivered, by the simple and foolproof operation of the control valve assembly 32, from the reservoir first syringe 12 to the push-draw second syringe 14 and then to the patient. At each stage of the process, unselected passageways of the valve assembly 32 remain totally isolated from used passageways so that the risk of administering embolic agents in an undesirable manner is minimized.

While the invention has been described in its preferred form or embodiment with some degree of particularity, it is understood that this description has been given only by way of example, and that numerous changes in the details of construction, fabrication, and use, including the combination and arrangement of parts, may be made without departing from the spirit and scope of the invention.

The invention claimed is:

1. A delivery system for the delivery of embolic agents to a patient, comprising:
 a control valve assembly interconnecting first, second, third and fourth conduits;
 a first syringe connected to the first conduit;
 a second syringe connected to the second conduit;
 a delivery catheter connected to the third conduit; and
 a third syringe connected to the fourth conduit;
 wherein the control valve assembly selectively moves between first, second, and third states under the control of a medical professional such that in the first state, the first and second conduits, and ultimately the first and second syringes, are isolated from the third and fourth conduits; while in the second state, the second and third conduits, as well as the second syringe and the delivery catheter, which is adapted to be connected to the patient, are isolated from the first conduit and fourth conduit; and while in the third state, the third and fourth conduits, as well as the patient and the third syringe, are isolated from the first conduit and second conduit.

2. The delivery system according to claim 1, wherein the control valve assembly includes a valve body having selectively aligned first, second, third and fourth passageways that define the first, second, third and fourth conduits, respectively.

3. The delivery system according to claim 2, wherein a stopcock is rotatably mounted within the valve body and includes an angled channel having a pair of communicably interconnected channel segments interconnected at an angle that is generally equivalent to the angle formed between each adjacent pair of non-aligned first, second, third and fourth passageways in the valve body such that the stopcock is rotatable to align the channel segments with a selected adjacent pair of the first, second, third and fourth passageways to permit communication between those passageways in a highly controlled manner.

4. The delivery system according to claim 3, wherein the stopcock is selectively adjusted between first, second and third positions.

5. The delivery system according to claim 4, wherein in the first position the channel segments communicably interconnect the first passageway defining the first conduit and the second passageway defining the second conduit for functioning in accordance with the first state.

6. The delivery system according to claim 5, wherein in the second position the channel segments communicably interconnect the second passageway defining the second conduit and the third passageway defining the third conduit for functioning in accordance with the second state.

7. The delivery system according to claim 6, wherein in the third position the channel segments communicably interconnect the third passageway defining the third conduit and the fourth passageway defining the fourth conduit for functioning in accordance with the third state.

8. The delivery system according to claim 1, wherein the third conduit includes a one-way valve for limiting flow to a single direction from a source to the patient and for preventing flow in an opposite direction.

9. The delivery system according to claim 8, wherein the fourth conduit includes a one-way valve and a fitting for selective and sealable connection of the third syringe.

* * * * *